United States Patent [19]

Varma et al.

[11] 4,018,757

[45] Apr. 19, 1977

[54] STEROIDAL[16α,17-C][2H]PYRROLES

[75] Inventors: Ravi K. Varma, Belle Mead; Christopher M. Cimarusti, Hamilton, both of N.J.

[73] Assignee: E. R. Squibb & Sons, Inc., Princeton, N.J.

[22] Filed: May 20, 1976

[21] Appl. No.: 688,207

[52] U.S. Cl. .................. 260/239.5; 260/397.45
[51] Int. Cl.² .................................. C07J 71/00
[58] Field of Search ...... Machine Searched Steroids

[56] References Cited

UNITED STATES PATENTS 3,349,084  10/1967  Ayer et al. ............... 260/239.55
3,359,287  12/1967  Babcock et al. ............ 260/397.4

*Primary Examiner*—Elbert L. Roberts
*Attorney, Agent, or Firm*—Lawrence S. Levinson; Merle J. Smith; Donald J. Barrack

[57] ABSTRACT

Steroids having the structure

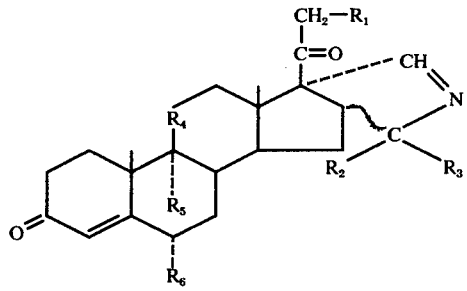

and the 1,2-dehydro derivatives thereof, wherein $R_1$ is hydrogen, hydroxy,

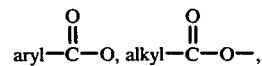

fluorine, chlorine, or bromine; $R_2$ is alkyl or aryl; $R_3$ is aryl, cyano, alkylcarbonyl, arylcarbonyl, alkoxycarbonyl, aryloxycarbonyl, alkylsulfonyl, or arylsulfonyl; $R_4$ is carbonyl, β-hydroxymethylene, β-chloromethylene or β-bromomethylene; $R_5$ is hydrogen, fluorine, chlorine or bromine; and $R_6$ is hydrogen, fluorine, or methyl; have useful antiinflammatory activity.

10 Claims, No Drawings

STEROIDAL[16α,17-C][2H]PYRROLES

BACKGROUND OF THE INVENTION

Many corticosteroids are known having heterocyclic rings fused in the 16- and 17-positions. U.S. Pat. No. 3,048,581, issued Aug. 7, 1962, discloses the preparation of acetals and ketals of 16,17-dihydroxypregnenes. U.S. Pat. No. 3,349,084, issued Oct. 24, 1967, discloses the preparation of steroidal [16,17-d]-2'-isoxazolines. These are, of course, only exemplary of the known steroids having a heterocyclic group fused in the 16,17-position.

The reaction of isonitriles containing an α-hydrogen atom with α,β-unsaturated carbonyl compounds in the presence of catalytic amounts of cuprous oxide is known; see, for example, Saegusa et al., *J. Org. Chem.*, 36, 3316 (1971). It is also known that the reaction can be catalyzed by bases such as sodium ethoxide. The use of these reactions in the field of steroid chemistry has resulted in the preparation of novel steroidal [16α,17-c] [2H]pyrroles.

SUMMARY OF THE INVENTION

Steroids having the formula

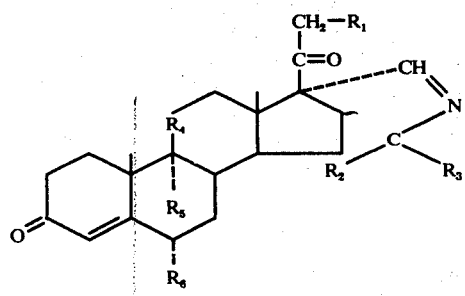

and the 1,2-dehydro derivatives thereof, can be used as topical and systemic antiinflammatory agents. In formula I, and throughout the specification, the symbols are as defined below:

$R_1$ can be hydrogen, hydroxy,

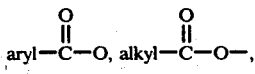

fluorine, chlorine, or bromine;
$R_2$ can be alkyl or aryl;
$R_3$ can be aryl, cyano, alkylcarbonyl, arylcarbonyl, alkoxycarbonyl, aryloxycarbonyl, alkylsulfonyl, or arylsulfonyl;
$R_4$ can be carbonyl, β-hydroxymethylene, β-chloromethylene, or β-bromomethylene;
$R_5$ can be hydrogen, fluorine, chlorine, or bromine; and
$R_6$ can be hydrogen, fluorine, or methyl.

The terms "alkyl" and "alkoxy", as used throughout the specification, whether alone or as part of a larger group, refer to groups having 1 to 6 carbon atoms.

The term "aryl", as used throughout the specification, whether by itself or as part of a larger group, refers to phenyl or phenyl substituted with fluorine, chlorine, bromine, nitro, cyano, alkyl or alkoxy groups. Phenyl and monosubstituted phenyl are preferred.

DETAILED DESCRIPTION OF THE INVENTION

The steroids of formula I are physiologically active substances which possess glucocorticoid and anti-inflammatory activity and hence can be used in lieu of known glucocorticoids in the treatment of rheumatoid arthritis, for which purpose they can be administered in the same manner as hydrocortisone, for example, the dosage being adjusted for the relative potency of the particular steroid. In addition, the steroids of this invention can be used topically in lieu of known glucocorticoids in the treatment of skin conditions such as dermatitis, psoriasis, sunburn, neurodermatitis, eczema, and anogenital pruritus.

When given orally, the compounds of this invention may be used in a dosage range of 0.1 to 200 milligrams, preferably 0.3 to 100 milligrams. If administered topically, the compounds of this invention may be used in the range of 0.01 to 5.0% by weight, preferably 0.05 to 2.0% by weight, in a conventional cream or lotion.

The steroids of this invention wherein $R_1$ is other than hydroxy and $R_4$ is carbonyl or β-hydroxymethylene can be prepared by reacting a steroid having the formula

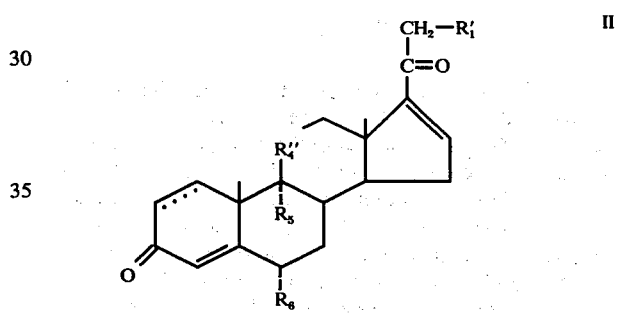

with an isonitrile having the formula

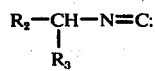

In formula II, and throughout the specification, the symbol $R'_1$ can be hydrogen,

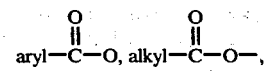

fluorine, chlorine, or bromine; $R'_4$ can be carbonyl or β-hydroxymethylene; and the dotted line in the 1,2-position of the steroid nucleus represents the optional presence of ethylenic unsaturation. The reaction can be run in the presence of a catalytic amount of cuprous oxide or of a base such as an alkali metal alkoxide (e.g., sodium ethoxide).

Those steroids of formula I (and the 1,2-dehydro derivatives thereof) wherein $R_1$ is other than hydroxy and $R_4$ is β-chloromethylene or β-bromomethylene can be prepared by first dehydrating a steroid having the formula

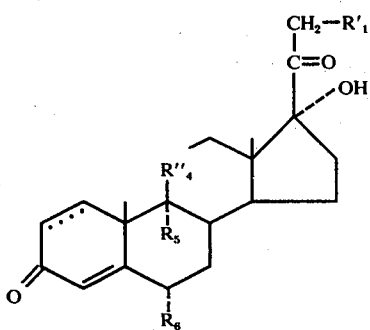

to yield a steroid having the formula

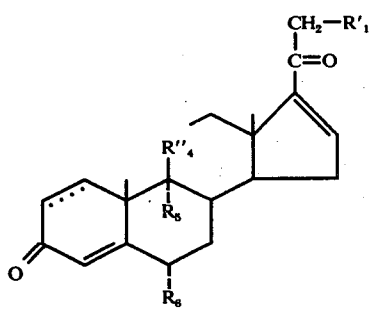

In formula IV, and throughout the specification, the symbol $R''_4$ can be β-chloromethylene or β-bromomethylene. The dehydration can be accomplished by treating a steroid of formula IV with an N-haloamide or N-haloimide and sulfur dioxide in a basic medium. It is desirable that the sulfur dioxide be present in at least an equimolar amount with respect to the haloamide or haloimide and preferable that an excess of sulfur dioxide be used. The preferred reagent is N-bromoacetamide, and pyridine is preferably utilized as the basic medium.

A steroid of formula V can be reacted with an isonitrile of formula III (using the procedure described above) to yield the steroids of formula I (or 1,2-dehydro derivatives thereof) wherein $R_1$ is other than hydroxy and $R_4$ is β-chloromethylene or β-bromomethylene.

Those steroids of formula I (and the 1,2-dehydro derivatives thereof) wherein $R_1$ is hydroxy can be prepared by saponification of a corresponding 21-acyloxy steroid using procedures well known in the art.

The isonitriles of formula III are obtainable using any one of the procedures known in the art. Exemplary procedures are disclosed in *Angew. Chem. Internat. Ed.*, 13 789 (1974) and *Angew. Chem. Internat. Ed.* 4, 472 (1965).

The following examples are specific embodiments of this invention.

EXAMPLE 1

9-Fluoro-3',4'-dihydro-11β-hydroxy-2'-methyl-3,20-dioxopregn-4-eno[16α,17-c][2H]pyrrole-2'-carboxylic acid, ethyl ester.

A solution of 9-fluoro-11β-hydroxypregna-4,16-diene-3,20-dione (346 mg) in a mixture of absolute ethanol (10 ml), dry tetrahydrofuran (4.0 ml) and ethyl-2-isocyanopropionate (140 mg) is stirred in an atmosphere of nitrogen, and sodium methoxide (15 mg) is added. When the solution is stirred at room temperature for 18 hours a significant reaction yielding two more polar compounds is noticed. Subsequent warming of the solution to 40° C for 4.0 hours did not cause further reaction. An additional amount of sodium methoxide (25 mg) is added. After stirring at room temperature for 20 hours further reaction is observed; however, some starting steroid is still present. At this point, the reaction is quenched by the addition of water and the products are isolated by extraction with ethyl acetate. The ethyl acetate extract is washed with water, dried and after evaporation the residue is subjected to preparative thin layer chromatography (tlc) on two 2.0 × 200 × 200 mm silica gel plates. After one development with chloroform-ethyl acetate (1:1), the three U.V. visible bands are isolated by extraction with chloroform-methanol (95:5) to afford in the order of increasing polarities 50, 100 and 300 mg of solids. The 50 mg is the starting material; the 100 mg is 16α-ethoxy-9-fluoro-11β-hydroxypregn-4-ene-3,20-dione; and the 300 mg is a mixture of two isomers of the title compounds. Though partial separation of the two isomers is possible by tlc on neutral alumina plates (chloroform-ethyl acetate (1:1), 4 or 5 developments), an attempt to separate these two by column chromatography on neutral alumina (60 g, activity II) is unsatisfactory. The appropriate fractions from the column are combined (235 mg). One crystallization from ethyl acetate-hexane gives the analytical specimen of the title compound (173 mg), melting point 203°–215° C.

Anal. Calc'd. for $C_{27}H_{36}FNO_5$: C, 68.47; H, 7.65; N, 2.96; F, 4.01; Found: C, 68.20; H, 7.47; N, 2.80; F, 3.95.

EXAMPLE 2

21-(Acetyloxy)-9-fluoro-3'-dihydro-11β-hydroxy-2'-methyl-3,20-dioxopregna-1,4-dieno[16α,17-c][2H]pyrrole-2'-carboxylic acid, ethyl ester (Isomers A and B)

A solution of 21-(acetyloxy)-9-fluoro-11β-hydroxypregna-1,4,16-triene-3,20-dione (804 mg) and ethyl-2-isocyanopropionate (267 mg) in dry tetrahydrofuran (20 ml) containing suspended cuprous oxide (25 mg) is refluxed under an atmosphere of nitrogen. In less than 2.0 hours the starting steroid disappears leaving two compounds of much higher polarity. The tetrahydrofuran is then evaporated, the residue was diluted with ethyl acetate and dried. The filtrate is evaporated and combined with the material (200 mg) from another similar reaction on a 0.4 mmole scale and the mixture (1.25 g) is absorbed on a column of neutral alumina (60 g, activity II). Elution of the column with chloroform removed some non-steroidal impurities and elution with chloroform-ethyl acetate mixtures (95:5 to 70:30) gives a mixture (450 mg) of the two isomers of the title compound. Further elution with ethyl acetate and ethyl acetate-methanol (8:2) gives a gum (100 mg) which is a mixture of several more polar compounds.

The 450 mg of material is applied on a preparative plate (2.0 × 200 × 200 mm) of silica gel, and the plate is developed three times with ethyl acetate-chloroform-methanol (80:19:1). The major less polar and more polar bands are extracted with chloroform-methanol (95:5) to isolate the two isomers as solids.

The solid from the less polar band is crystallized once from ethyl acetate to afford the analytical specimen of the title compound, Isomer A (154 mg), melting point 260°–261° C (dec.).

Anal. Calc'd. for $C_{29}H_{36}FNO_7$: C, 65.77; H, 6.85; N, 2.64; F, 3.50; Found: C, 65.51; H, 6.81; N, 2.54; F, 3.56.

The solid from the more polar band is crystallized once from ethyl acetate to yield the analytical specimen of the title compound Isomer B (142 mg), melting point 265°–266.5° C (dec.).

EXAMPLE 3

21-(Acetyloxy)-9-fluoro-3',4'-dihydro-11β-hydroxy-2'-methyl-2'-phenyl-3,20-dioxopregna-1,4-dieno[16α,17-c][2H]pyrrole A mixture of 21-(acetyloxy)-9-fluoro-11β-hydroxypregna-1,4,16-triene-3,20-dione (1 g), DL-1-phenylethylisocyanide (720 mg) and cuprous oxide (80 mg) in 50 ml of tetrahydrofuran is refluxed under nitrogen for 3 days. Some tetrahydrofuran (25 ml) is then distilled off and the refluxing was continued for another 2 days. The solvent is then removed in vacuo to give a foam (1.4 g). This is dissolved in chloroform and chromatographed on a 40 g-silica gel column. Elution with chloroform and ethyl acetate-chloroform (5:95, 10:90 and 15:85) gives two isomers, A (540 mg) and B (72 mg). Isomer A is crystallized from ethyl acetate-hexane to give 303 mg of solid, melting point 304°–306° C.

Anal. Calc'd. for $C_{32}H_{36}FNO_5$: C, 72.02; H, 6.80; N, 2.63; F, 3.56; Found: C, 72.07; H, 6.80; N, 2.63; F, 3.60.

EXAMPLES 4–8

Following the procedure of Example 2, but substituting the steroid listed in column I for 21-(acetyloxy)-9-fluoro-11β-hydroxypregna-1,4,16-triene-3,20-dione and the compound listed in column II for ethyl-2-isocyanopropionate, yields the steroid listed in column III.

EXAMPLE 9

21-Acetyloxy-11β-bromo-9-fluoro-3',4'-dihydro-2'-methyl-2'-phenyl-3,20-dioxopregn-4-eno[16α,17-c][2H]pyrrole

A.

21-Acetyloxy-11β-bromo-9-fluoropregna-4,16-diene-3,20-dione

A solution of 21-acetyloxy-11β-bromo-9-fluoro-17-hydroxypregn-4-ene-3,20-dione (4.0 g) in pyridine (10 ml) is cooled to 10° C. A solution of N-bromosuccinimide (2.0 g) in pyridine (7.0 ml) is added at 10° C and the mixture is warmed to room temperature and stirred for 10 minutes. It is recooled to 10° C and a solution of sulfur dioxide (2.2 g) in pyridine (10 ml) is added. The mixture is warmed to room temperature and then added slowly, with stirring into 1N hydrochloric acid (300 ml). The title compound is separated and purified.

B.

21-Acetyloxy-11β-bromo-9-fluoro-3',4'-dihydro-2'-methyl-2'-phenyl-3,20-dioxopregn-4-eno[16α,17-c][2H]pyrrole 21-Acetyloxy-11β-bromo-9-fluoropregna-4,16-diene-3,20-dione is reacted with DL-1-phenylethylisocyanide in the presence of cuprous oxide, as described in Example 3, to yield the title compound.

EXAMPLES 10 and 11

Following the procedure of Example 9, but substituting the steroid listed in column I for 21-acetyloxy-11β-bromo-9-fluoro-17-hydroxypregn-4-ene-3,20-dione and the compound listed in column II for DL-1-phenylethylisocyanide, yields the steroid listed in column III.

| Example | Column I | Column II | Column III |
| --- | --- | --- | --- |
| 4 | 11β-hydroxypregna-4,16-diene-3,20-dione | phenyl-2-isocyanopropionate | 11β-hydroxy-3',4'-dihydro-2'-methyl-3,20-dioxopregn-4-eno[16α,17-c][2H]-pyrrole-2'-carboxylic acid, phenyl ester |
| 5 | 21-benzoyloxy-9-fluoro-11β-hydroxypregna-1,4,16-triene-3,20-dione | 1-phenylethylisocyanide | 21-benzoyloxy-9-fluoro-3',4'-dihydro-11β-hydroxy-2'-methyl-2'-phenyl-3,20-dioxopregna-1,4-dieno[16α,17-c][2H]pyrrole |
| 6 | 21-chloro-6α,9-difluoro-11β-hydroxypregna-1,4,16-triene-3,20-dione | methyl-2-isocyanopropionate | 21-chloro-6α,9-difluoro-3',4'-dihydro-11β-hydroxy-2'-methyl-3,20-dioxopregna-1,4-dieno[16α,17-c][2H]pyrrole-2'-carboxylic acid, methyl ester |
| 7 | 21-bromo-9-fluoropregna-4,16-diene-3,11,20-trione | 1-(methylcarbonyl)-ethylisocyanide | 21-bromo-9-fluoro-3',4'-dihydro-2'-methyl-2'-methylcarbonyl-3,11,20-trioxopregn-4-eno[16α,17-c][2H]pyrrole |
| 8 | 21-acetyloxy-9-fluoropregna-1,4,16-triene-3,11,20-trione | 1-(phenylcarbonyl)-ethylisocyanide | 21-acetyloxy-9-fluoro-3',4'-dihydro-2'-methyl-2'-phenylcarbonyl-3,11,20-trioxopregna-1,4-dieno[16α,17-c][2H]pyrrole |

| Example | Column I | Column II | Column III |
| --- | --- | --- | --- |
| 10 | 21-acetyloxy-9,11β-difluoro-17-hydroxypregna-1,4-diene-3,20-dione | ethyl-2-isocyanopropionate | 21-acetyloxy-9,11β-difluoro-3',4'-dihydro-2'-methyl-3,20-dioxopregna-1,4-dieno[16α,17-c][2H]pyrrole-2'-carboxylic acid, ethyl ester |
| 11 | 21-acetyloxy-9,11β-dichloro-17-hydroxypregna-1,4-diene-3,20-dione | 1-(phenylsulfonyl)-ethylisocyanide | 21-acetyloxy-9,11β-dichloro-3',4'-dihydro-2'-methyl-2'-phenylsulfonyl-3,20-dioxopregna-1,4-dieno[16α,17-c][2H]pyrrole |

EXAMPLE 12

9-Fluoro-3′,4′-dihydro-11β,21-dihydroxy-2′-methyl-3,20-dioxopregna-1,4-dieno[16α,17-c][2H]pyrrole-2′-carboxylic acid, ethyl ester A solution of 21-acetyloxy-9-fluoro-3′,4′-dihydro-11β-hydroxy-2′-methyl-3,20-dioxopregna-1,4-dieno[16α,17-c][2H]-pyrrole-2′-carboxylic acid, ethyl ester (1.0 g, see example 2) in 300 ml of methanol is cooled to 0° C and 30 ml of 10% potassium carbonate solution is added. After 15 minutes, 1.3 g of acetic acid is added and the mixture is concentrated in vacuo, diluted with water and extracted with chloroform to yield the title compound.

What is claimed is:

1. A steroid having the formula

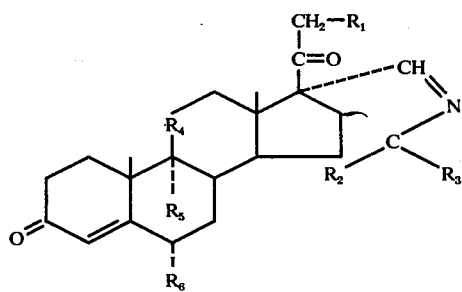

or a 1,2-dehydro derivative thereof, wherein $R_1$ is hydrogen, hydroxy,

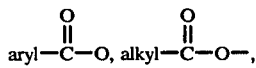

fluorine, chlorine or bromine; $R_2$ is alkyl or aryl; $R_3$ is aryl, cyano, alkylcarbonyl, arylcarbonyl, alkoxycarbonyl, aryloxycarbonyl, alkylsulfonyl, or arylsulfonyl; $R_4$ is carbonyl, β-hydroxymethylene, β-chloromethylene, or β-bromomethylene; $R_5$ is hydrogen, fluorine, chlorine or bromine; and $R_6$ is hydrogen, fluorine or methyl; wherein aryl is phenyl or phenyl substituted with fluorine, chlorine, bromine, nitro, cyano, alkyl or alkoxy; and alkyl and alkoxy are groups having 1 to 6 carbon atoms.

2. A steroid in accordance with claim 1 wherein $R_1$ is

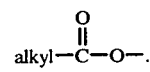

3. A steroid in accordance with claim 1 wherein $R_2$ is alkyl and $R_3$ is alkoxycarbonyl.

4. A steroid in accordance with claim 1 wherein $R_2$ is alkyl and $R_3$ is aryl.

5. A steroid in accordance with claim 1 wherein $R_4$ is β-hydroxymethylene.

6. A steroid in accordance with claim 1 wherein $R_5$ is fluorine.

7. A steroid in accordance with claim 1 wherein $R_6$ is hydrogen.

8. The steroid in accordance with claim 1 having the name 9-fluoro-3′,4′-dihydro-11β-hydroxy-2′-methyl-3,20-dioxopregn-4-eno[16α,17-c][2H]pyrrole-2′-carboxylic acid, ethyl ester.

9. The steroid in accordance with claim 1 having the name 21-(acetyloxy)-9-fluoro-3′,4′-dihydro-11β-hydroxy-2′-methyl3,20-dioxopregna-1,4-dieno[16α,17-c][2H]pyrrole-2′-carboxylic acid, ethyl ester.

10. The steroid in accordance with claim 1 having the name 21-(acetyloxy)-9-fluoro-3′,4′-dihydro-11β-hydroxy-2′-methyl-2′-phenyl-3,20-dioxopregna-1,4-dieno[16α,17-c][2H]pyrrole.

* * * * *